United States Patent [19]

Winston et al.

[11] Patent Number: 4,623,536

[45] Date of Patent: Nov. 18, 1986

[54] SODIUM BICARBONATE CONTAINING TOOTHPASTE

[75] Inventors: Anthony E. Winston, East Brunswick; Raymond Brown, Bridgewater; Norman Usen, Marlboro; Anthony Ansaldi, Mt. Arlington, all of N.J.

[73] Assignee: Church & Dwight Co., Inc., Piscataway, N.J.

[21] Appl. No.: 744,497

[22] Filed: Jun. 13, 1985

[51] Int. Cl.$^4$ .......................... A61K 7/16; A61K 7/18
[52] U.S. Cl. .......................................... 424/49; 424/52
[58] Field of Search .................................. 424/49-58

[56] References Cited

U.S. PATENT DOCUMENTS

| | | | |
|---|---|---|---|
| 1,082,681 | 12/1913 | Danner | 424/49 |
| 1,112,180 | 9/1914 | Westenfelter | 167/93 |
| 1,297,494 | 3/1919 | Rhein | 424/55 |
| 1,716,035 | 2/1927 | Donchi | 424/55 |
| 1,943,467 | 2/1932 | Bley | 424/50 |
| 2,024,146 | 12/1935 | Crowther | 424/49 |
| 2,035,267 | 3/1936 | Fleischmann | 424/53 |
| 2,128,917 | 9/1938 | Crocker | 167/93 |
| 2,196,150 | 4/1940 | Heald et al. | 424/57 |
| 2,196,154 | 4/1940 | Schullrud | 424/49 |
| 2,216,816 | 10/1940 | Kuever | 424/57 |
| 2,519,665 | 8/1950 | Klippert | 424/57 |
| 2,550,207 | 4/1951 | Tainter et al. | 424/49 |
| 2,723,217 | 11/1955 | Gershon et al. | 424/57 |
| 2,820,000 | 1/1958 | Menzies | 424/49 |
| 2,941,926 | 6/1960 | Sallmann et al. | 424/57 |
| 3,003,919 | 10/1961 | Broge | 424/49 |
| 3,060,098 | 10/1962 | Gershon | 424/57 |
| 3,325,368 | 6/1967 | Wood | 424/57 |
| 3,330,732 | 7/1967 | Muhler | 424/49 |
| 3,450,813 | 6/1969 | Muhler | 424/49 |
| 3,647,381 | 3/1972 | Reiter | 424/49 |
| 3,935,304 | 1/1976 | Januszewski et al. | 424/49 |
| 3,935,305 | 1/1976 | Delaney et al. | 424/49 |
| 3,937,321 | 2/1976 | Delaney et al. | 424/49 |
| 3,937,803 | 2/1976 | Delaney et al. | 424/49 |
| 3,937,804 | 2/1976 | Delaney et al. | 424/52 |
| 3,943,240 | 3/1976 | Delaney et al. | 424/49 |
| 3,947,570 | 3/1976 | Pensak et al. | 424/49 |
| 3,957,968 | 5/1976 | Cordon | 424/57 |
| 3,989,813 | 11/1976 | Januszewski et al. | 424/54 |
| 4,060,599 | 11/1977 | Cordon | 424/49 |
| 4,089,943 | 5/1978 | Roberts et al. | 424/49 |
| 4,102,992 | 7/1978 | Davis | 424/49 |
| 4,132,770 | 1/1979 | Barth | 424/49 |
| 4,144,322 | 3/1979 | Cordon et al. | 424/49 |
| 4,160,022 | 7/1979 | Delaney et al. | 424/49 |
| 4,168,301 | 9/1979 | Pugh et al. | 424/49 |
| 4,276,287 | 6/1981 | Cabardo | 424/49 |
| 4,344,931 | 8/1982 | Aguilar | 424/49 |
| 4,547,362 | 10/1985 | Winston et al. | 424/49 |

FOREIGN PATENT DOCUMENTS

| | | |
|---|---|---|
| 1413643 | 11/1975 | United Kingdom . |
| 1413642 | 11/1975 | United Kingdom . |
| 1413641 | 11/1975 | United Kingdom . |
| 2112642A | 7/1983 | United Kingdom . |

OTHER PUBLICATIONS

Lehne et al., Clinical Preventive Dentistry 5(1):17-18 Jan.-Feb. 1983, Abrasivity of Sodium Bicarbonate.

*Primary Examiner*—Shep K. Rose
*Attorney, Agent, or Firm*—Stiefel, Gross, Kurland & Pavane

[57] ABSTRACT

A toothpaste containing at least 60% sodium bicarbonate particles as the sole abrasive, at least 30% of the sodium bicarbonate having particle sizes of less than 25 microns. Humectants, thickening agents, fluoridating agents, flavors, sweeteners and other conventional adjuvants may also be included in the toothpaste.

10 Claims, No Drawings

SODIUM BICARBONATE CONTAINING TOOTHPASTE

TECHNICAL FIELD

This invention relates to a sodium bicarbonate containing toothpaste. More particularly, this invention relates to a toothpaste containing sodium bicarbonate particles as the sole abrasive agent therein.

BACKGROUND OF THE INVENTION

Many different dentifrice compositions are known for cleaning, whitening, and preserving the teeth. Of these known dentifrices, many include high contents of water-insoluble abrasives which aid in removing plaque and retarding stain build-up on the teeth. However, since the ultimate goal of any oral hygiene regimen is preservation of the teeth, it is widely accepted that dentifrice compositions should include the least abrasive material necessary to remove plaque and stain.

The use of sodium bicarbonate as an abrasive in dentifrices has previously been proposed. While sodium bicarbonate has been described in the literature as an ingredient of both tooth powders (see, for example, Danner U.S. Pat. No. 1,082,681; Crowther U.S. Pat. No. 2,024,146; Cabardo U.S. Pat. No. 4,276,287; and Winston et al U.S. application Serial No. 628,855 filed July 9, 1984, owned by the assignee of this invention) and toothpastes (see, for example, Januszewski et al U.S. Pat. No. 3,935,304; and Delaney et al U.S. Pat. Nos. 3,935,305; 3,937,321; 3,937,803; 3,937,804; 3,943,240; and 4,160,022), prior to this date it has met with limited commercial success.

Tooth powders generally contain only abrasives, flavors, sweeteners, and surfactants. On the other hand, toothpastes generally contain, in addition to the abrasive material, humectants, thickeners and water, as well as surfactants, flavors, and sweeteners. Both forms of dentifrice may also contain additional ingredients for special functional or esthetic reasons, for example, fluoridating or coloring agents. In view of the distinct nature of tooth powder and toothpaste formulations and, particularly, the presence of humectants, thickeners and water in toothpastes but not tooth powders, an abrasive which is suitable for use in a tooth powder may not be suitable for use in a toothpaste and, conversely, an abrasive which is suitable in a toothpaste may not be suitable in a tooth powder.

In general, sodium bicarbonate is a desirable abrasive for dentifrice compositions because it is low in abrasion and imparts an exceptionally clean, fresh feel to the mouth. Sodium bicarbonate particles are relatively soft as compared to most conventional abrasive materials used in dentifrice compositions. Thus, the American Dental Association has recommended that if only a slight degree of abrasion is necessary to keep from staining, baking soda is usually a satisfactory abrasive. *Accepted Dental Therapeutics*, pp.340–41 (38th Ed., 1979).

Heretofore, low abrasivity has been associated with poor stain removal properties. Secondary abrasives have, therefore, frequently been incorporated in sodium bicarbonate containing toothpaste formulations to enhance their stain removal properties. See, for example, the aforesaid Delaney et al patents, which disclose incorporating secondary, insoluble abrasives such as silica, chalk, alumina, zirconium silicate, or alumino silicates in amounts of 5–25%, or more, of the toothpaste formulations described therein. Similarly, Januszewski et al discloses a sodium bicarbonate based toothpaste additionally comprising from 0.1 to 5.0% titanium dioxide to enhance the polishing ability of the formulation.

The need for a secondary abrasive to improve the polishing ability of a sodium bicarbonate based dentifrice may be obviated by increasing the level of sodium bicarbonate in the formulation. This can be effective in a tooth powder, where there is essentially no practical limit to the level of sodium bicarbonate which can be incorporated into the product. However, high levels of conventional bicarbonate abrasives in toothpaste formulations impart excessively high viscosities, and prevent mixing during manufacture. Additionally, the dispensibility of such compositions is unacceptable. At the maximum possible levels (about 60–65%) at which conventional bicarbonate abrasives can be utilized in toothpastes, while still maintaining an acceptable consistency, the polishing ability of the formulation is insufficient due to the mild abrasivity of this material. Thus, previous attempts to achieve acceptable cleaning power in a toothpaste formulation by incorporating therein high levels of sodium bicarbonate as the sole abrasive have been unsatisfactory.

To avoid the undesirable effects generally associated with high levels of abrasive, the amount of abrasive included in known toothpaste formulations is generally limited to between 40 and 50%. See, for example, the Delaney et al patents mentioned above, and Crocker U.S. Pat. No. 2,128,917 which discloses incorporating sodium bicarbonate passing a #200 mesh sieve (74 microns) in an amount of up to 50% of a toothpaste formulation.

Formulation stability is also a frequent problem with sodium bicarbonate containing toothpastes. Sodium bicarbonate is unstable in aqueous solution and releases carbon dioxide gas. As a result, the pH of bicarbonate based toothpastes increases during the requisite degassing procedure. It is desirable that dentifrice compositions have a pH close to the neutral range (e.g., pH of 5–9) to avoid damaging sensitive oral tissues. Moreover, in fluoride containing formulations, an increased pH may cause reduced fluoride uptake by tooth enamel. See, for example, the aforesaid Delaney et al U.S. Pat. No. 3,943,240 (column 1, lines 32–34) and U.S. Pat. No. 3,937,803 (column 9, lines 15–21), which caution that degassing be discontinued before the pH of the composition increases by one pH unit, even though degassing may be incomplete.

Another problem encountered in formulating a sodium bicarbonate based toothpaste is that sodium bicarbonate is not always compatible with other abrasive materials in the formulation. See, for example, Delaney et al U.S. Pat. No. 3,943,240 at column 2, lines 58–62.

Thus, it is among the objects of the present invention to provide a sodium bicarbonate based toothpaste containing higher amounts of bicarbonate than in previous formulations, which toothpaste is effective in removing plaque and retarding stain build-up on the teeth without deleterious abrasion of tooth enamel, cementum or dentin, and which toothpaste substantially overcomes the formulation problems previously encountered, such as poor dispensibility, consistency, stability, and increased pH on degassing.

Other objects and advantages of the invention will be apparent from the following description of preferred embodiments thereof.

DISCLOSURE OF THE INVENTION

In accordance with the present invention, a toothpaste is provided comprising sodium bicarbonate as the sole abrasive material in an amount of at least about 60% by weight of the formulation, and wherein at least about 30% by weight of the sodium bicarbonate is of a particle size less than 25 microns. Toothpaste formulations prepared in accordance with this invention provide cleaning and stain removal properties comparable to the leading commercial toothpastes. The toothpaste hereof has the further advantage of being low in abrasion despite its high content of abrasive material, as well as possessing desirable consistency and texture. Also, the sodium bicarbonate toothpaste of the invention is stable on storage, even at elevated temperatures. Unlike existing sodium bicarbonate toothpastes, the toothpaste of this invention has virtually no tendency to excessively increase in pH on degassing.

It has now been found that, contrary to expectation, higher levels of sodium bicarbonate—e.g., from about 60–75% by weight—can be incorporated in toothpastes if finer particle size baking soda is used. Toothpaste formulations including such an abrasive, i.e., a bicarbonate in which at least 30%, preferably from about 40 to 100%, of its particles have sizes of from about 5 to 25 microns, provide adequate stain removal without the addition of any further abrasive. Moreover, the finer particle size bicarbonate abrasives employed herein do not adversely affect slurry viscosity during toothpaste formulation. In fact, the viscosity decreases as particle size decreases. Thus, a sodium bicarbonate based toothpaste incorporating the particular sized bicarbonate according to this invention, exhibits both good cleaning properties and formulating and dispensing characteristics.

A particularly significant advantage of the formulation of the invention is the ability to provide satisfactory stain removal properties without having to include a second abrasive therein. Surprisingly, the low abrasivity generally associated with sodium bicarbonate based toothpastes is not increased in toothpastes formulated according to the invention, even though stain removal properties are improved. Thus a further, although unexpected advantage of the toothpaste of the present invention is that, while providing adequate stain and plaque removal, it is generally lower in abrasivity than commercial dentifrices. Low abrasion to dental enamel and dentin is of considerable importance for maintaining and preserving the teeth.

A further, and surprising, advantage of the toothpaste of the invention is that, unlike sodium bicarbonate toothpaste formulations previously reported, the pH has no tendency to rise during degassing. In fact, no increase in pH of the present formulation is recorded, even if degassing is continued for extended periods, e.g., 1 hour. Thus, unlike the toothpastes disclosed in the aforesaid Delaney et al patents, wherein degassing was discontinued prior to complete deaeration to avoid pH increases of greater than one pH unit, in preparing the toothpaste of the present invention deaeration can proceed to completion.

The toothpaste formulation of the invention also includes at least a humectant and a thickener. Examples of humectants include glycerol, propylene glycol, sorbitol, polyethylene glycols (generally of formula $H(OC_2H_4)_nOH$), and other materials known to those skilled in the art. The humectant may be present in the toothpaste in an amount of up to about 35%, preferably in an amount of about 8 to 25%, by weight of the toothpaste formulation. Suitable thickeners include sodium carboxymethylcellulose, xanthan gum, methyl cellulose, hydroxyethyl cellulose, carrageen, gum karaya, gum tragacanth, gum arabic, colloidal complex magnesium aluminum silicates (e.g. "Veegum", manufactured by R.T. Vanderbilt Co.), and sodium alginate. The thickener is incorporated in the toothpaste in an amount of up to about 3%, preferably within the range of about 0.3 to 1.5%, by weight of the toothpaste.

The toothpastes of the present invention preferably contain other ingredients in addition to sodium bicarbonate, a humectant, and a thickening agent. The toothpaste may thus contain water in an amount necessary to achieve formulation of the toothpaste, e.g., from about 0 to 25% by weight. Additional ingredients may include surfactants, flavoring agents, sweeteners, and fluoridating agents, as recognized by those skilled in the art.

Suitable surfactants include anionic surfactants such as the sulfates of long chain ($C_8$–$C_{18}$) alcohols e.g. sodium lauryl sulfate or sodium tridecyl sulfate, the sulfates or sulfonates of monoglycerides e.g. sodium lauroyl glyceryl sulfate or sodium coconut monoglyceride sulfonate; the sulfonates of succinic esters e.g. sodium dioctyl sulfosuccinate; the alkyl sulfoacetates such as sodium lauryl sulfoacetate or sodium coconut sulfoacetate; the salts of sulfoacetic acid amidified with amino ethyl long chain fatty acid esters such as sodium sulfocolaurate; the amides formed from higher fatty acids with short chain amino acids such as sodium lauroyl sarcosinate or sodium methyl lauroyl tauride and soaps such as the sodium, potassium or triethanolamine salts of fatty acids. Similarly non-ionic surfactants may be used such as the ethoxylated sugar esters of the higher fatty acids for example ethoxylated sorbitan monostearate and ethoxylated glycol monostearate. Also amphoteric surfactants such as the mono or dicarboxylated imidazoline derivatives of fatty acids such as sodium lauryl dicarboxy imidazoline or sodium coconut dicarboxy imidazoline may be used. Cationic surfactants may also be used in the invention. These materials may impart significant antibacterial action to the product. Examples are benzyl dimethyl stearyl ammonium chloride and cetyl pyridinium chloride. The surfactant(s) are present in the toothpaste in an amount of up to about 5.0%, preferably within the range of about 0.3% to 2.0%, by weight of the toothpaste.

The flavor of a sodium bicarbonate containing toothpaste is affected by the particle size of the sodium bicarbonate. Generally, the saltiness of the toothpaste increases as the particle size decreases. However, the effect of small particle size sodium bicarbonate in a toothpaste formulation is not as pronounced as in tooth powders. It is believed that the presence of the humectant and thickening agents in the toothpaste formulation retard bicarbonate dissolution in the mouth and thus reduce the adverse saltiness. It should, however, be understood that this hypothesis does not, in any way, limit the scope of the present invention.

Moreover, much of the saltiness can be masked by the addition of optional flavoring agents and/or sweeteners to the toothpaste formulation. Suitable flavoring agents include the flavoring oils, for example, peppermint, spearmint, menthol, wintergreen, clove, cinnamon, lemon, orange, methylsalicylate, licorice, or eucalyptus. The flavoring agent may be present in the toothpaste in an amount up to about 5.0%, preferably in an amount within the range of about 0.3 to 2.0% by weight of the toothpaste. Suitable sweeteners include sodium saccharin, sodium or calcium cyclamate, aspartame, and other sweeteners known to those skilled in the art. The sweetener may be present in the toothpaste in an amount of up to about 5.0%, preferably about 0.3 to 2.0%, by weight of the toothpaste. It should be noted that humectants, e.g. sorbitol, may sweeten the formulation to some degree. However, the amount of humectant present in the composition is not included in the range of sweetener set forth above.

The toothpastes of the present invention may additionally contain a fluoridating agent to aid in preventing dental caries. Many fluoridating agents suitable for use in dentrifrice compositions are known. Among these are sodium, potassium, lithium or ammonium fluorides, organic amine fluorides, monofluorophosphate salts such as sodium, potassium, lithium and ammonium monofluorophosphate, sodium fluorosilicate, sodium fluorozirconate, and other materials well known to those skilled in the art. The fluoridating agents are present in an effective but non-toxic amount, e.g., in amounts of up to about 2.0%, and preferably in an amount to provide a fluoride level equivalent to about 1000 ppm of fluoride ion.

BEST MODE FOR CARRYING OUT THE INVENTION

The preferred toothpaste formulations of the invention comprises about 62.0 to 75.0% by weight of sodium bicarbonate, at least about 30% of which has a particle size under 25 microns, desirably about 5 to 25 microns. Preferably, the fine particles comprise about 40.0 to 100.0% of the sodium bicarbonate included in the formulation. Of the remaining sodium bicarbonate content, about 65.0-100.0% has a particle size of from 25 to 210 microns, preferably from about 25 to 88 microns.

It is particularly preferred to incorporate the following ingredients in the bicarbonate-containing toothpaste of the invention:

|  | % By Weight |
|---|---|
| sodium bicarbonate | 62-76 |
| Less than 5 microns | 0-5 |
| 5-25 microns | 35-100 |
| 25-88 microns | 0-60 |
| humectant | 8-25 |
| (preferably glycerol or mixtures with polyethylene glycol of molecular weight 400 (e.g. Carbowax 400) | |
| thickener | 0.3-1.5 |
| (preferably sodium carboxymethyl cellulose) | |
| surfactant | 0.2-1.0 |
| (preferably sodium lauryl sulfate and/or sodium lauroyl sarcosinate | |
| flavoring agent | 0.3-2.0 |
| sweetener | 0.3-2.0 |
| (preferably saccharin) | |
| fluoridating agent | 0.22-0.76 |
| (preferably sodium fluoride/ sodium monofluorophosphate) | |

The preferred toothpastes of the present invention are prepared by first mixing the thickener with the humectant. A water solution containing the sweetener, surfactant and fluoride is added to the thickener-humectant mixture. Then, the sodium bicarbonate is stirred into the mixture. Finally, the flavor oil is added. The composition is then deaerated under vacuum, e.g., at about 26-30 inches of mercury, the vacuum being released every few minutes to improve release of the trapped gases, and then reapplied. The deaeration process is generally completed in about 20 minutes.

The following examples illustrate particularly preferred embodiments of the toothpaste of the present invention. In the examples all parts and percentages are given by weight.

EXAMPLES 1-3

TEXTURE AND DISPENSING CHARACTERISTICS OF TOOTHPASTES CONTAINING 62% SODIUM BICARBONATE

62% Sodium Bicarbonate

Examples of the sodium bicarbonate containing toothpaste of the invention were prepared from the following formulation. The examples were compared with controls based on the same formulation but containing bicarbonate components having differing particle size distributions in order to show the effect of the bicarbonate particle size distribution on the texture and dispensing pressure of the resulting product.

|  | Formulation I |
|---|---|
| Sodium bicarbonate | 62.0 |
| Water | 18.13 |
| Glycerine | 17.1 |
| Carboxymethylcellulose | 0.75 |
| Sodium fluoride | 0.22 |
| Sodium lauryl sulfate | 0.3 |
| Sodium lauroyl sarcosinate | 0.3 |
| Flavor | 0.7 |
| Saccharin | 0.5 |
|  | 100.0% |

Dispensing pressure and texture were evaluated. Dispensing pressure was determined by measuring the pressure required to eject a 26 mm strip of toothpaste through a 7 mm orifice. Dispensing pressure of a toothpaste composition is of concern because it is directly related to the dispensing of the paste from the tube and onto a toothbrush. Texture was evaluated visually using the following rating system: 1—very creamy smooth; 2—creamy smooth; 3—creamy, slightly gritty; 4—dry, slightly gritty; 5—dry, gritty.

Examples 1, 2 and 3 representing variations of Formulation I within the scope of the invention, were compared with Controls A and B, which are variations of Formulation I containing sodium bicarbonate having differing particle size distributions and "Crest" toothpaste (Control C). It should be noted that control B contains the commercial grade of sodium bicarbonate (baking soda) available to consumers, i.e, grade 1. The results are summarized in Table I:

TABLE I
COMPARATIVE TEXTURE AND DISPENSING CHARACTERISTICS OF TOOTHPASTES CONTAINING 62% SODIUM BICARBONATE HAVING VARYING PARTICLE SIZE DISTRIBUTIONS

| | CONTROL | | | EXAMPLE | | |
|---|---|---|---|---|---|---|
| | A | B | C ("Crest")* | 1 | 2 | 3 |
| More than 149 microns | 92.5 | 0.5 | | 0 | 0 | 0 |
| 89–149 microns | 6.5 | 19.5 | | 0 | 13 | 0 |
| 45–88 microns | 1.0 | 50 | | 15 | 33 | 0 |
| 25–44 microns | 0 | 18 | | 45 | 12 | 0 |
| Less than 25 microns | 0 | 12 | | 40 | 42 | 100 |
| Initial dispensing pressure (lbs.) | 5.25 | 2.37 | 3.12 | 2.0 | 2.25 | 2.50 |
| Dispensing pressure (lbs.), after 3 weeks at 125° F. | 8.2 | 4.75 | 3.50 | 3.1 | 3.6 | 3.0 |
| Dispensing pressure (lbs.), after 9 weeks at 125° F. | 23.1 | 6.0 | 4.0 | 3.8 | 3.8 | 3.3 |
| Initial texture rating | 5 | 4 | 1 | 1 | 3 | 1 |
| Texture rating after 9 weeks at 125° F. | 5 | 4 | 1 | 4 | 3 | 2 |

*Contains sodium fluoride in a base of sorbitol (humectant), water, hydrated silica (abrasive), trisodium phosphate (buffer), sodium lauryl sulfate (surfactant), flavor, titanium dioxide (to improve color, and as a second abrasive), sodium phosphate (buffer), xanthan gum (thickening agent), Carbomer 940 (an acrylic type of polymeric thickening/emulsifying agent), sodium saccharin (sweetener) and FD&C Blue #1 (colorant).

The above comparisons demonstrate that when the level of smaller particle size sodium bicarbonate crystals is increased, the dispensing pressure is lower and the smoothness of the toothpaste is greater, than when larger bicarbonate particles are employed in the formulation. As can be seen from the data presented in Table I, Examples 1, 2 and 3 prepared in accordance with the present invention had low dispensing pressures which were comparable with "Crest" (Control C). Additionally, Examples 1, 2 and 3 had acceptable creamy textures.

In contrast Control A, incorporating coarse crystals of sodium bicarbonate, had an unacceptably high dispensing pressure especially on aging. Control B, a toothpaste prepared with a quantity of fine crystals of sodium bicarbonate, below the level of the invention, had an initially acceptable dispensing pressure. However, on aging the dispensing pressure increased beyond an acceptable level. Both Controls A and B had unacceptably dry textures.

EXAMPLES 4–5
TEXTURE AND DISPENSING CHARACTERISTICS OF TOOTHPASTES CONTAINING 70% SODIUM BICARBONATE

Further toothpastes were prepared, and dispensing pressure and texture comparisons performed, employing compositions prepared from the following formulations containing 75% (Example 4) and 70% (Example 5) sodium bicarbonate, respectively: the results, which are set forth in Table II, show that even at sodium bicarbonate levels of 70% and above, low dispensing pressures and acceptable consistencies are obtained.

TABLE II
COMPARATIVE TEXTURE AND DISPENSING CHARACTERISTICS OF TOOTHPASTES CONTAINING 70% AND 75% SODIUM BICARBONATE HAVING VARYING PARTICLE SIZE DISTRIBUTIONS

| | EXAMPLE | |
|---|---|---|
| | 4 | 5 |
| Sodium bicarbonate | 75 | 70 |
| Water | 13.08 | 18.08 |
| Glycerin | 9.38 | 9.38 |
| Xanthan gum | 0.25 | 0.25 |
| Carboxymethylcellulose | 0.25 | 0.25 |
| Sodium Fluoride | 0.24 | 0.24 |
| Sodium Lauryl Sulfate | 0.3 | 0.3 |
| Sodium Lauroyl Sarcosinate | 0.3 | 0.3 |
| Flavor | 0.7 | 0.7 |
| Saccharin | 0.5 | 0.5 |
| Particle size of bicarbonate used | | |
| more than 149 microns | 0 | 0 |
| 89–149 microns | 12 | 11 |
| 45–88 microns | 30 | 29 |
| 25–44 microns | 11 | 10 |
| Less than 25 microns | 47 | 50 |
| Initial dispensing pressure | NT* | 4.2 |
| Dispensing pressure (lbs.) after 1 week at 125° F. | 4.8 | 5.7 |
| Dispensing pressure (lbs.) after 3 weeks at 125° F. | NT* | 3.8 |

*NT — Not tested

EXAMPLES 6–9
STAIN REMOVAL AND ABRASIVE PROPERTIES OF TOOTHPASTES CONTAINING 65% SODIUM BICARBONATE

Tests were run to illustrate the stain removal and abrasion properties of sodium bicarbonate based toothpastes. Examples 6 through 9 and Controls D, E and F incorporated the ingredients specified in Formulation II below. Examples 6 through 9 contain varying bicarbonate particle size distributions in accordance with the invention.

The stain removal properties of the various toothpaste compositions were evaluated using a simulated stain removal test. Ceramic tiles were stained with concentrated tea solution, and the stain was fixed by dipping the tiles in ferrous sulfate. A slurry of test product (2 parts) and water (1 part) was placed on each test tile and the tile was brushed in a Gardner straight line washability machine for 50 cycles. The tiles were then rinsed and dried. Stain removal was determined by comparing the reflectance before and after brushing.

Examples 6 through 9 were compared with Controls D, E and F, and with "Crest" (Control C) for stain removal efficiency. The results are set forth below.

|  | Formulation II |
|---|---|
| Sodium Bicarbonate | 65 |
| Water | 16.63 |
| Glycerin | 15.60 |
| Carboxymethylcellulose | 0.75 |
| Sodium Fluoride | 0.22 |
| Sodium Lauryl Sulfate | 0.30 |
| Sodium Lauroyl Sarcosinate | 0.30 |
| Flavor | 0.70 |
| Saccharin | 0.50 |

TABLE III

COMPARATIVE STAIN REMOVAL AND ABRASIVE PROPERTIES OF TOOTHPASTES CONTAINING 65% SODIUM BICARBONATE HAVING VARYING PARTICLE SIZE DISTRIBUTIONS

|  | CONTROL | | | | EXAMPLE | | | |
|---|---|---|---|---|---|---|---|---|
|  | D | E | F | C† | 6 | 7 | 8 | 9 |
| More than 149 microns | 0.5 | 0 | 0.5 |  | 0 | 0 | 0 | 0 |
| 89–149 microns | 19.5 | 11 | 16.5 |  | 0 | 6 | 14 | 0 |
| 45–88 microns | 50 | 35 | 43 |  | 15 | 16 | 34 | 0 |
| 25–44 microns | 18 | 30 | 15 |  | 45 | 6 | 12 | 0 |
| Less than 25 microns | 12 | 24 | 25 |  | 40 | 72 | 40 | 100 |
| Increase in Reflectance (Higher value equals better stain removal | 13.2* | 19.8* | 22.7* | 31.0° | 27.3° | 27.6° | 28.0° | 31.0° |

† "Crest"
*Worse performance than Control C, and Examples 6–9 (>95% Confidence Level)
°Not significantly different than Control C.

The stain removal comparisons demonstrate that stain removal properties generally increase with an increase in the proportion of the sodium bicarbonate particles having sizes less than 25 microns. Controls D, E and F, all containing 25% or less sodium bicarbonate particles sized below 25 microns, performed significantly poorer in the stain removal tests than Examples 6–9, and Control C.

EXAMPLES 10–14

STAIN REMOVAL PROPERTIES OF TOOTHPASTES CONTAINING 62% SODIUM BICARBONATE AND INCORPORATING VARYING WATER TO HUMECTANT RATIOS

Another stain removal comparison was performed to determine whether variations in the water to humectant ratio would affect the stain removal properties of toothpastes formulated in accordance with the invention. Examples 10 through 14 and Controls G, H and I incorporated the composition of Formulation III, set forth below. Stain removal was evaluated as described in Examples 6–9, above.

Formulation III

| Sodium bicarbonate | 62.0 |
|---|---|
| Water + Glycerin* | 35.23 |
| Carboxymethylcellulose | 0.75 |
| Sodium fluoride | 0.22 |
| Sodium lauryl Sulfate | 0.3 |
| Sodium lauroyl Sarcosinate | 0.3 |
| Flavor | 0.70 |
| Saccharin | 0.50 |
|  | 100.00 |

*Ratios as set forth in Table IV.

TABLE IV

COMPARATIVE STAIN REMOVAL PROPERTIES OF TOOTHPASTES CONTAINING 62% SODIUM BICARBONATE HAVING DIFFERENT PARTICLE SIZE DISTRIBUTIONS AND VARYING WATER TO HUMECTANT RATIOS

|  | CONTROL | | | | EXAMPLE | | | | |
|---|---|---|---|---|---|---|---|---|---|
|  | G | H | I | C† | 10 | 11 | 12 | 13 | 14 |
| More than 149 microns | 92.5 | 0.5 | 0.5 |  | 0 | 0 | 0 | 0 | 0 |
| 89–149 microns | 6.5 | 19.5 | 19.5 |  | 13 | 0 | 13 | 13 | 0 |
| 45–88 microns | 1.0 | 50 | 50 |  | 33 | 0 | 33 | 33 | 0 |
| 25–44 microns | 0 | 18 | 18 |  | 12 | 0 | 12 | 12 | 0 |
| Less than 25 microns | 0 | 12 | 12 |  | 42 | 100 | 42 | 42 | 100 |
| Water/Glycerin Ratio | 1.1/1 | 1.3/1 | 0.6/1.0 |  | 1.3/1.0 | 0.6/1.0 | 1.1/1.1 | 0.6/1.0 | 1.3/1.0 |
| Increase in Reflectance | 5.6* | 14.7* | 14.9* | 22.4 | 18.4° | 19.0° | 20.3° | 21.7° | 23.0° |

† "Crest"
*Significantly worse performance than Control C and Examples 12–14 (>95% Confidence Level)
°Not significantly different than Control C.

The above comparisons generally confirm that increasing the quantity of sodium bicarbonate particles under 25 microns in the composition improves stain removal. Thus, it is possible to formulate toothpastes having sodium bicarbonate as the sole abrasive, without sacrificing the stain removal achieved by commercially available products such as "Crest". Additionally, Table IV demonstrates that varying the water to humectant ratio does not significantly affect stain removal. Examples 10-14, prepared in accordance with the invention, have stain removal properties equivalent to that of the "Crest" control.

EXAMPLES 15-16

STAIN REMOVAL PROPERTIES OF TOOTHPASTES CONTAINING VARYING PROPORTIONS OF SODIUM BICARBONATE

Comparisons of stain removal properties of toothpastes containing various total amounts of sodium bicarbonate show that if sodium bicarbonate is used as the sole abrasive high levels (65%—Example 15; or 75%—Example 16) are required to obtain the desired cleaning capacity.

Stain removal comparisons were performed in the manner previously described. The results, which are summarized in Table V, show that stain removal generally increases with a corresponding increase in the amount of sodium bicarbonate, provided the requisite level of fine particles of baking soda is maintained. As shown, at least 60% sodium bicarbonate is necessary to achieve stain removal equivalent to the commercial dentifrice.

Moreover, and contrary to expectation, solely using sodium bicarbonate particles under 25 microns in size, but at a total percentage of less than 60%, does not significantly improve stain removal properties. Thus, a sodium bicarbonate based toothpaste containing baking soda as the sole abrasive only achieves the stain removal performance of a commercial dentifrice, if at least 60% sodium bicarbonate, with greater than 30% of the bicarbonate particles being smaller than 25 microns is included in the formulation.

TABLE V

COMPARATIVE STAIN REMOVAL CHARACTERISTICS OF TOOTHPASTES CONTAINING VARYING TOTAL AMOUNTS OF SODIUM BICARBONATE

|  | CONTROL | | | EXAMPLE | |
|---|---|---|---|---|---|
|  | J | K | L | 15 | 16 |
| Sodium Bicarbonate | 40 | 40 | 50 | 65 | 75 |
| Water + Glycerin (Ratio 1:1) | 56.78 | 46.98 | 32.28 | 22.48 | 56.78 |
| Carboxymethylcellulose | 1.20 | 1.20 | 1.00 | 0.70 | 0.50 |
| Sodium Fluoride | 0.22 | 0.22 | 0.22 | 0.22 | 0.22 |
| Sodium Lauryl Sulfate | 0.30 | 0.30 | 0.30 | 0.30 | 0.30 |
| Sodium Lauroyl Sarcosinate | 0.30 | 0.30 | 0.30 | 0.30 | 0.30 |
| Flavor | 0.70 | 0.70 | 0.70 | 0.70 | 0.70 |
| Saccharin | 0.50 | 0.50 | 0.50 | 0.50 | 0.50 |
| PARTICLE SIZE DISTRIBUTION OF BICARBONATES USED | | | | | |
| More than 149 microns | 0 | 0 | 0 | 0 | 0 |
| 89-149 microns | 0 | 14 | 14 | 14 | 14 |
| 45-88 microns | 0 | 34 | 34 | 34 | 34 |
| 24-44 microns | 0 | 12 | 12 | 12 | 12 |
| Less than 25 microns | 100 | 40 | 40 | 40 | 40 |
| STAIN REMOVAL CHARACTERISTICS | | | | | |
|  | J | K | L | Control C ("Crest") | 15 | 16 |
| Increase in Reflectance | 15.4* | 13.4* | 16.8* | 23.0 | 24.4° | 29.2** |

*Significantly poorer than Examples 15 and 16, and Control C. (>92% Confidence Level)
°Same as Control C ("Crest")
**Significantly better than Control C ("Crest") (>95% Confidence Level)

EXAMPLES 17-18

ABRASIVE CHARACTERISTICS OF TOOTHPASTES CONTAINING 62% SODIUM BICARBONATE, As Compared With Commercial Toothpaste Formulations The abrasivity of Examples 17 and 18 was compared with the abrasive characteristics of Controls M, N and O. Examples 17 and 18, and Control M, were prepared from Formulation I (set forth above), with Examples 17 and 18 containing a sodium bicarbonate particle size distribution according to the present invention. Controls C, N and O were commercial toothpastes ("Crest", "Aim" and "Colgate"); the latter two formulations contain calcium pyrophosphate as the abrasive therein.

In the abrasion studies, the test toothpastes were compared for relative enamel and dentin abrasivity using the method of J. J. Hefferren ("A Laboratory Method for Assessment of Dentifrice Abrasivity," J.Dent.Research 55, 563-573, 1976). Relative enamel abrasivity was determined by abrading the crowns of freshly extracted irradiated human teeth, using slurries of the test compositions. The enamel removed was quantitated by the level of radioactive phosphorus abraded into the slurry. Similarly, relative dentin abrasivity was measured by abrading the roots of freshly extracted irradiated teeth, and determining the amount of radioactive dentin removed. The results were also compared with that of a calcium pyrophosphate control.

Slurries of Examples 17 and 18 and Control M were prepared using 25 grams of paste in 50 ml. water. A 10 g control slurry of calcium pyrophosphate in 50 ml. of 0.5% aqueous carboxymethylcellulose was given an arbitrary abrasivity value of 100.

The results demonstrate that there is no significant difference in dentin or enamel abrasivity between the test toothpastes containing sodium bicarbonate levels in accordance with the invention (Examples 17 and 18) and that toothpaste (Control M) formulated with less than 30% of the baking soda particles smaller than 25 microns. Also, as can be seen, the toothpaste compositions of the invention are significantly lower in dentin abrasivity than the commercial products (Controls C, N and O).

TABLE VI

COMPARATIVE ABRASIVE CHARACTERISTICS OF TOOTHPASTES CONTAINING SODIUM BICARBONATES HAVING VARYING PARTICLE SIZE DISTRIBUTION, WITH COMMERCIAL CONTROL TOOTHPASTE FORMULATIONS

|  | CONTROL | | | | EXAMPLE | |
| --- | --- | --- | --- | --- | --- | --- |
|  | C ("Crest") | M | N ("Aim")[1] | O | 17 ("Colgate")[2] | 18 |
| More than 149 microns |  | 0.5 |  |  | 0 | 0 |
| 89-149 microns |  | 19.5 |  |  | 0 | 13 |
| 45-88 microns |  | 50 |  |  | 15 | 33 |
| 25-44 microns |  | 18 |  |  | 45 | 12 |
| Less than 25 microns |  | 12 |  |  | 40 | 42 |
| Relative dentin abrasivity | 71 | 44* | 64 | 63 | 43* | 46* |
| Relative enamel abrasivity | 21 | 9** | 10 | 12** | 10** | 11** |

*Lower abrasivity than controls C, N and O. (>95% Confidence Level)
**Lower abrasivity than controls C and N. (>95% Confidence Level)
[1] Aim contains sodium monofluorophosphate in a base of sorbitol, hydrated silica, PEG 32, water, sodium lauryl sulfate, SD alcohol 38B, flavor, cellulose gum, sodium saccharin, sodium benzoate, FD&C Blue #1, D&C Yellow #10.
[2] Colgate contains sodium monofluorophosphate in a base of dicalcium phosphate dihydrate, water, glycerin, sodium lauryl sulfate, cellulose gum, flavor, sodium benzoate, tetro-sodium pyrophosphate, sodium saccharin.

EXAMPLES 19-20

ABRASIVE CHARACTERISTICS OF TOOTHPASTES CONTAINING 40% AND 100% SODIUM BICARBONATE AS COMPARED WITH "CREST"

Two additional sodium bicarbonate based toothpastes prepared in accordance with the present invention were compared with "Crest", for relative abrasivity to enamel and dentin. These results show that a sodium bicarbonate toothpaste wherein all the sodium bicarbonate particles are smaller than 25 microns, has significantly lower abrasivity than "Crest".

|  | Example 19 | Example 20 |
| --- | --- | --- |
| Sodium bicarbonate | 62 | 65 |
| Water | 18.13 | 16.63 |
| Glycerin | 17.1 | 15.6 |
| Carboxymethylcellulose | 0.75 | 0.75 |
| Sodium Fluoride | 0.22 | 0.22 |
| Sodium Lauryl Sulfate | 0.3 | 0.3 |
| Sodium Lauroyl Sarcosinate | 0.3 | 0.3 |
| Flavor | 0.7 | 0.7 |
| Saccharin | 0.5 | 0.5 |

TABLE VII

ABRASIVE CHARACTERISTICS OF TOOTHPASTES CONTAINING SODIUM BICARBONATES HAVING VARYING PARTICLE SIZE DISTRIBUTIONS, AS COMPARED WITH "CREST"

|  | CONTROL C ("Crest") | EXAMPLE | |
| --- | --- | --- | --- |
|  |  | 19 | 20 |
| More than 149 microns |  | 0 | 0 |
| 89-149 microns |  | 0 | 14 |
| 45-88 microns |  | 0 | 34 |
| 22-24 microns |  | 0 | 12 |
| Less than 25 microns |  | 100 | 40 |
| Relative dentin abrasivity | 90 | 47* | 47* |
| Relative enamel abrasivity | 24 | 18 | 21 |

*Lower abrasivity than control (>95% Confidence Level)

EXAMPLES 21-23

DEGASSING CHARACTERISTICS OF TOOTHPASTES CONTAINING SODIUM BICARBONATES HAVING VARYING PARTICLE SIZE DISTRIBUTIONS

As previously discussed, the toothpastes of this invention can be totally degassed without significant increase in pH. Tests were run comparing the pH, before and after degassing, of three toothpaste compositions of the invention. The results, which are summarized in Table VIII below, show that there is no significant change in pH after degassing has been completed.

TABLE VIII

COMPARISON OF pH BEFORE AND AFTER DEGASSING OF FORMULATIONS CONTAINING SODIUM BICARBONATES HAVING THE PARTICLE SIZE DISTRIBUTION OF THE INVENTION

|  | EXAMPLE | | |
| --- | --- | --- | --- |
|  | 21 | 22 | 23 |
| Sodium Bicarbonate | 62 | 62 | 62 |
| Water | 19.91 | 18.13 | 16.78 |
| Glycerin | 15.32 | 17.1 | 18.54 |
| Carboxymethylcellulose | 0.75 | 0.75 | 0.75 |
| Sodium Fluoride | 0.22 | 0.22 | 0.22 |
| Sodium Lauryl Sulfate | 0.3 | 0.3 | 0.3 |
| Sodium Lauroyl Sarcosinate | 0.3 | 0.3 | 0.3 |
| Flavor | 0.7 | 0.7 | 0.7 |
| Saccharin | 0.5 | 0.5 | 0.5 |
| Particle Size of bicarbonate used |  |  |  |
| More than 149 microns | 0 | 0 | 0 |
| 89-149 microns | 13 | 0 | 13 |
| 45-88 microns | 33 | 0 | 33 |
| 25-44 microns | 12 | 0 | 12 |
| Less than 25 microns | 42 | 100 | 42 |
| pH before degassing | 9.15 | 9.3 | 9.0 |
| pH after degassing | 8.9 | 8.9 | 9.1 |

It will be understood that the preferred toothpaste compositions of the invention described herein are illustrative only, and should not be construed as limiting the present invention.

What is claimed is:

1. In a toothpaste containing an abrasive, a humectant and a thickening agent, the improvement comprising sodium bicarbonate as the sole abrasive, the sodium bicarbonate being incorporated in the toothpaste in an amount of at least 60% by weight, and at least 30% by weight of the sodium bicarbonate having a particle size of less than 25 microns.

2. The toothpaste according to claim 1, wherein the humectant is selected from the group consisting of glycerol, propylene glycol, sorbitol and polyethylene glycols.

3. The toothpaste according to claim 1, wherein the thickening agent is selected from the group consisting of sodium carboxymethylcellulose, xanthan gum, methyl cellulose, hydroxyethyl cellulose, carrageen, gum karaya, gum tragacanth, gum arabic, and sodium alginate.

4. The toothpaste according to claim 1 further comprising a surfactant.

5. The toothpaste according to claim 1, further comprising from 0.3 to 5.0% by weight of a flavoring agent.

6. The toothpaste according to claim 1, further comprising from 0.3 to 5.0% by weight of a non-humectant sweetener.

7. A sodium bicarbonate based toothpaste comprising from 60 to 75% by weight sodium bicarbonate, at least 30% of said sodium bicarbonate having a particle size of less than 25 microns; from 5 to 25% by weight of a humectant; from 0.3 to 3.0% by weight of a thickener; from 0.3 to 5.0% by weight of a surfactant; from 0.3 to 5.0% by weight of a flavoring agent; and from 0.3 to 5.0% by weight of a sweetener.

8. The toothpaste of claim 8, wherein from 25% to 100% of the sodium bicarbonate has a particle size of from 5 to 25 microns, and from 60 to 100% of the sodium bicarbonate has a particle size of from 25 to 210 microns.

9. The toothpaste of claim 7, wherein the humectant is selected from the group consisting of glycerol, propylene glycol, sorbitol, and polyethylene glycols.

10. The toothpaste of claim 7, wherein the thickener is selected from the group consisting of sodium carboxymethylcellulose, xanthan gum, methyl cellulose, hydroxyethyl cellulose, carrageen, gum karaya, gum tragacanth, gum arabic, and sodium alginate.

* * * * *